(12) United States Patent
Gunderson

(10) Patent No.: US 9,572,990 B2
(45) Date of Patent: Feb. 21, 2017

(54) SYSTEM AND METHOD FOR IDENTIFYING LEAD DISLODGEMENT

(75) Inventor: Bruce D. Gunderson, Plymouth, MN (US)

(73) Assignee: Medtronic, Inc., Minneapolis, MN (US)

(*) Notice: Subject to any disclaimer, the term of this patent is extended or adjusted under 35 U.S.C. 154(b) by 187 days.

(21) Appl. No.: 13/546,602

(22) Filed: Jul. 11, 2012

(65) Prior Publication Data

US 2014/0018873 A1    Jan. 16, 2014

(51) Int. Cl.
| A61N 1/37 | (2006.01) |
| A61N 1/365 | (2006.01) |
| A61B 5/0402 | (2006.01) |
| A61B 5/00 | (2006.01) |
| A61N 1/08 | (2006.01) |

(52) U.S. Cl.
CPC ........... *A61N 1/3702* (2013.01); *A61B 5/0402* (2013.01); *A61B 5/7203* (2013.01); *A61N 1/371* (2013.01); *A61N 2001/083* (2013.01)

(58) Field of Classification Search
CPC .............. A61N 1/3702; A61N 1/371; A61N 2001/083; A61B 5/0402; A61B 5/7203
USPC ................ 600/521; 607/6, 9, 17, 18, 23, 27
See application file for complete search history.

(56) References Cited

U.S. PATENT DOCUMENTS

| 3,602,215 A | 8/1971 | Parnell |
| 5,344,430 A | 9/1994 | Berg et al. |
| 5,354,316 A | 10/1994 | Keimel |
| 5,455,186 A | 10/1995 | Inn |
| 5,549,646 A | 8/1996 | Katz et al. |
| 5,593,431 A | 1/1997 | Sheldon |
| 5,704,365 A * | 1/1998 | Albrecht ............... A61B 5/0408 128/901 |
| 5,713,932 A | 2/1998 | Gillberg |
| 5,755,742 A | 5/1998 | Schuelke et al. |
| 5,776,168 A | 7/1998 | Gunderson |
| 5,814,088 A | 9/1998 | Paul et al. |
| 5,897,577 A | 4/1999 | Cinbis et al. |
| 5,910,120 A * | 6/1999 | Kim .................... A61N 1/3706 600/509 |
| 5,957,861 A | 9/1999 | Combs et al. |
| 6,067,469 A | 5/2000 | Kim |
| 6,195,584 B1 * | 2/2001 | Hill et al. ........................ 607/28 |
| 6,393,316 B1 | 5/2002 | Gillberg et al. |

(Continued)

FOREIGN PATENT DOCUMENTS

WO    2006119136 A1    11/2006

OTHER PUBLICATIONS

Veltmann, C., et al. "Fatal Inappropriate ICD Shock", J Cariovasc Electrophysiol; vol. 18, pp. 326-328, Mar. 2007.

(Continued)

*Primary Examiner* — Christopher D Koharski
*Assistant Examiner* — Pamela M Bays

(57) ABSTRACT

A medical device system and method for detecting cardiac lead dislodgement measures intervals between sensed cardiac events for detecting an event interval pattern including at least one short event interval consecutively followed by a long event interval. Responsive to detecting the event interval pattern, a cardiac signal amplitude associated with a detected short event interval is measured. Dislodgement of the cardiac lead is detected in response to the measured amplitude.

9 Claims, 6 Drawing Sheets

(56) References Cited

U.S. PATENT DOCUMENTS

| | | | |
|---|---|---|---|
| 6,445,952 B1 * | 9/2002 | Manrodt | A61N 1/37 607/28 |
| 6,490,486 B1 | 12/2002 | Bradley | |
| 6,599,242 B1 | 7/2003 | Combs et al. | |
| 6,807,439 B2 | 10/2004 | Edwards | |
| 7,047,083 B2 | 5/2006 | Gunderson et al. | |
| 7,120,493 B2 | 10/2006 | Propp et al. | |
| 7,242,978 B2 | 7/2007 | Cao et al. | |
| 7,266,409 B2 | 9/2007 | Gunderson | |
| 7,277,757 B2 | 10/2007 | Casavant et al. | |
| 7,289,851 B2 | 10/2007 | Gunderson et al. | |
| 7,391,979 B2 | 6/2008 | Yamaguchi et al. | |
| 7,454,249 B1 | 11/2008 | Bornzin et al. | |
| 7,515,961 B2 | 4/2009 | Germanson et al. | |
| 7,747,320 B1 | 6/2010 | Kroll et al. | |
| 7,783,354 B2 | 8/2010 | Gunderson | |
| 7,873,410 B2 | 1/2011 | Cho | |
| 7,974,690 B2 | 7/2011 | Kracker | |
| 8,099,166 B2 | 1/2012 | Schüller et al. | |
| 8,131,357 B2 | 3/2012 | Bradley | |
| 8,200,322 B2 | 6/2012 | Ousdigian et al. | |
| 8,200,330 B2 | 6/2012 | Kroll et al. | |
| 8,355,783 B2 | 1/2013 | Goetz et al. | |
| 8,391,979 B2 | 3/2013 | Kuhn et al. | |
| 8,396,543 B2 | 3/2013 | Hoeppner et al. | |
| 8,401,629 B2 | 3/2013 | Stadler et al. | |
| 8,543,206 B2 | 9/2013 | Naware et al. | |
| 8,626,293 B2 | 1/2014 | Bornzin et al. | |
| 8,738,111 B2 | 5/2014 | Sweeney et al. | |
| 9,008,773 B2 | 4/2015 | Gunderson | |
| 2002/0120307 A1 | 8/2002 | Jorgenson et al. | |
| 2002/0161295 A1 | 10/2002 | Edwards | |
| 2005/0096708 A1 | 5/2005 | Seim | |
| 2005/0137636 A1 | 6/2005 | Gunderson et al. | |
| 2006/0116733 A1 | 6/2006 | Gunderson | |
| 2006/0116747 A1 | 6/2006 | Eick | |
| 2006/0155338 A1 | 7/2006 | Mongeon | |
| 2006/0235476 A1 | 10/2006 | Gunderson et al. | |
| 2006/0264777 A1 | 11/2006 | Drew | |
| 2007/0100407 A1 | 5/2007 | Armstrong | |
| 2007/0293903 A1 | 12/2007 | Bohn et al. | |
| 2008/0161870 A1 | 7/2008 | Gunderson | |
| 2008/0161872 A1 | 7/2008 | Gunderson | |
| 2008/0215110 A1 | 9/2008 | Gunderson | |
| 2008/0269627 A1 * | 10/2008 | Cho et al. | 600/521 |
| 2009/0270938 A1 * | 10/2009 | Pei et al. | 607/28 |
| 2009/0292331 A1 * | 11/2009 | Gunderson et al. | 607/5 |
| 2010/0023084 A1 | 1/2010 | Gunderson | |
| 2010/0106209 A1 * | 4/2010 | Gunderson et al. | 607/17 |
| 2010/0114222 A1 | 5/2010 | Gunderson et al. | |
| 2010/0286542 A1 | 11/2010 | Indla et al. | |
| 2011/0009918 A1 | 1/2011 | Bornzin et al. | |
| 2011/0054558 A1 | 3/2011 | Gunderson et al. | |
| 2011/0098766 A1 | 4/2011 | Gunderson | |
| 2011/0319957 A1 | 12/2011 | Naware et al. | |
| 2012/0004699 A1 | 1/2012 | Bobgan et al. | |
| 2012/0109235 A1 | 5/2012 | Sheldon et al. | |
| 2012/0143278 A1 | 6/2012 | Ryu et al. | |
| 2012/0158089 A1 | 6/2012 | Bocek et al. | |
| 2012/0179056 A1 | 7/2012 | Moulder et al. | |
| 2012/0191153 A1 | 7/2012 | Swerdlow et al. | |
| 2013/0013038 A1 | 1/2013 | Miller | |
| 2013/0253352 A1 | 9/2013 | Bornzin et al. | |
| 2014/0018873 A1 | 1/2014 | Gunderson | |
| 2014/0350620 A1 | 11/2014 | Gunderson et al. | |
| 2014/0350621 A1 | 11/2014 | Gunderson et al. | |

OTHER PUBLICATIONS

Leong et al., "Unrecognized Failure of a Narrow Caliber Defibrillation Lead: The Role of Defibrillation Threshold Testing in Identifying an Unprotected Individual", PACE, vol. 00, 2012, 2 pages.

* cited by examiner

SYSTEM AND METHOD FOR IDENTIFYING LEAD DISLODGEMENT

FIELD OF THE DISCLOSURE

The disclosure relates generally to implantable medical devices and, in particular, to an apparatus and method for identifying dislodgement of an implantable cardiac lead.

BACKGROUND

Implantable medical devices (IMDs), including pacemakers and implantable cardioverter-defibrillators (ICDs), record cardiac electrogram (EGM) signals for sensing cardiac events, e.g. P-waves and R-waves. Episodes of bradycardia, tachycardia and/or fibrillation are detected from the sensed cardiac events and responded to as needed with pacing therapy or high-voltage cardioversion/defibrillation therapy. Reliable detection and treatment of potentially life-threatening ventricular tachycardia (VT) and ventricular fibrillation (VF) requires reliable sensing of cardiac signals. Dislodgement or dislocation of a cardiac lead carrying electrodes for sensing EGM signals can result in erroneous sensing of cardiac signals, leading to improper detection of the cardiac rhythm and inappropriate delivery or withholding of pacing or shock therapy. While ventricular lead dislodgement is rare, if it does occur inappropriate shock therapy and proarrhythmia caused by unnecessary therapy could result, or a necessary or optimal therapy may not be delivered, such as bradycardia pacing or anti-tachycardia pacing. Accordingly, it is desirable to provide an implantable medical device and associated cardiac lead system capable of detecting lead dislodgement.

DETAILED DESCRIPTION

In the following description, references are made to illustrative embodiments. It is understood that other embodiments may be utilized without departing from the scope of the disclosure.

Figure 1:
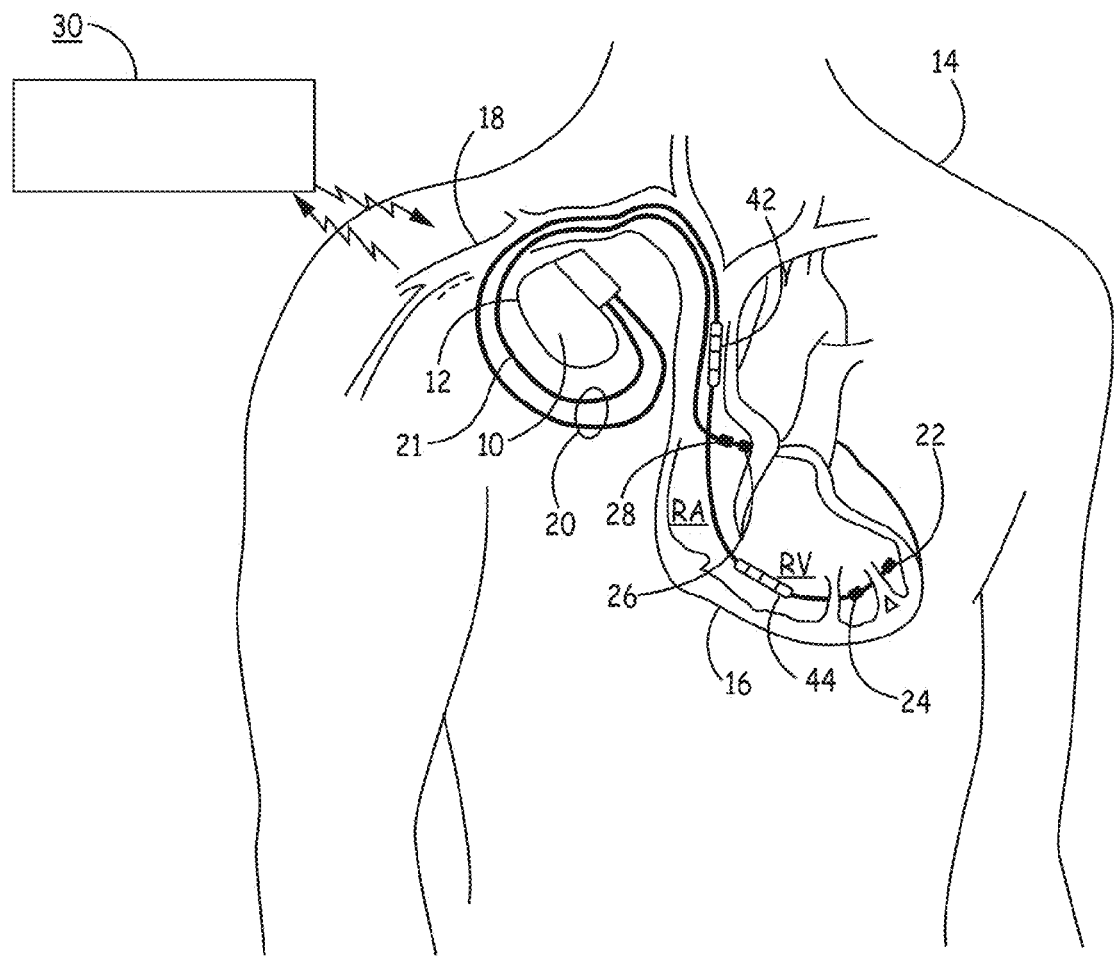
FIG. 1 is a schematic diagram of an implantable medical device system according to one embodiment.

FIG. 1 is a schematic diagram of an implantable medical device system 8 according to one embodiment. A system 8 for sensing cardiac events (e.g. P-waves and R-waves) and detecting tachyarrhythmia episodes includes IMD 10 and leads 20 and 21. IMD 10 may be embodied as an ICD capable of delivering pacing, cardioversion and defibrillation therapy to the heart 16 of a patient 14. Ventricular lead 20 and atrial lead 21 are electrically coupled to IMD 10 and extend into the patient's heart 16 via a vein 18. Ventricular lead 20 includes electrodes 22 and 24 shown positioned in the patient's right ventricle (RV) for sensing ventricular EGM signals and pacing in the RV. Atrial lead 21 includes electrodes 26 and 28 positioned in the patient's right atrium (RA) for sensing atrial EGM signals and pacing in the RA.

Lead 20 additionally carries high voltage coil electrodes 42 and 44 used to deliver cardioversion and defibrillation shock pulses. The leads 20 and 21 are used to acquire intracardiac EGM signals from the patient 14 and to deliver therapy in response to the acquired data. IMD 10 is shown as a dual chamber ICD, but in some embodiments, system 8 may be embodied as a multi-chamber system including a coronary sinus lead extending into the right atrium, through the coronary sinus and into a cardiac vein to position electrodes along the left ventricle (LV) for sensing LV EGM signals and delivering pacing pulses to the LV.

In some examples, ventricular lead 20 is anchored along the right ventricular apex or the intraventricular septum by a fixation member (not shown), such as tines positioned at the distal end of lead 20 in the vicinity of electrode 22 or a helical screw, which may also serve as electrode 22. Use of a fixation member generally anchors the position of ventricular lead 20 in the RV. However, on rare occasions, lead 20 may become dislodged from the ventricular myocardium and shift or migrate within the ventricle or toward the right atrium. When this occurs, the EGM signal received by IMD 10 from electrodes 22 and 24 will change due to the altered location of electrodes 22 and 24. Techniques for detecting cardiac lead dislodgement, particularly dislodgement of a ventricular lead, will be described herein.

These techniques will be described with regard to a right ventricular lead but may be applicable to a coronary sinus lead positioned along a cardiac vein for sensing left ventricular EGM signals. Additionally or alternatively, the techniques described herein may be adapted for use in identifying dislocation of an atrial lead. A right atrial lead, such as lead 21, may become dislocated and advance closer or into the right ventricle, for example.

IMD circuitry configured for performing the methods described herein and associated battery(ies) are housed within a sealed housing 12. Housing 12 may be conductive so as to serve as an electrode for use as an indifferent electrode during pacing or sensing or as an active electrode during defibrillation. As such, housing 12 is also referred to herein as "housing electrode" 12.

EGM signal data, cardiac rhythm episode data, and lead dislodgement data acquired by IMD 10 can be transmitted to an external device 30. External device 30 may be embodied as a programmer, e.g. used in a clinic or hospital to communicate with IMD 10 via wireless telemetry. External device 30 may be coupled to a remote patient monitoring system, such as Carelink®, available from Medtronic, Inc., Minneapolis, Minn. Device 30 is used to program commands or operating parameters into IMD 10 for controlling IMD function and to interrogate IMD 10 to retrieve data, including device operational data as well as physiological data accumulated in IMD memory. Examples of communication techniques used by IMD 10 and external device 30 include low frequency or radiofrequency (RF) telemetry, which may be an RF link established via Bluetooth, WiFi, or MICS.

Figure 2:
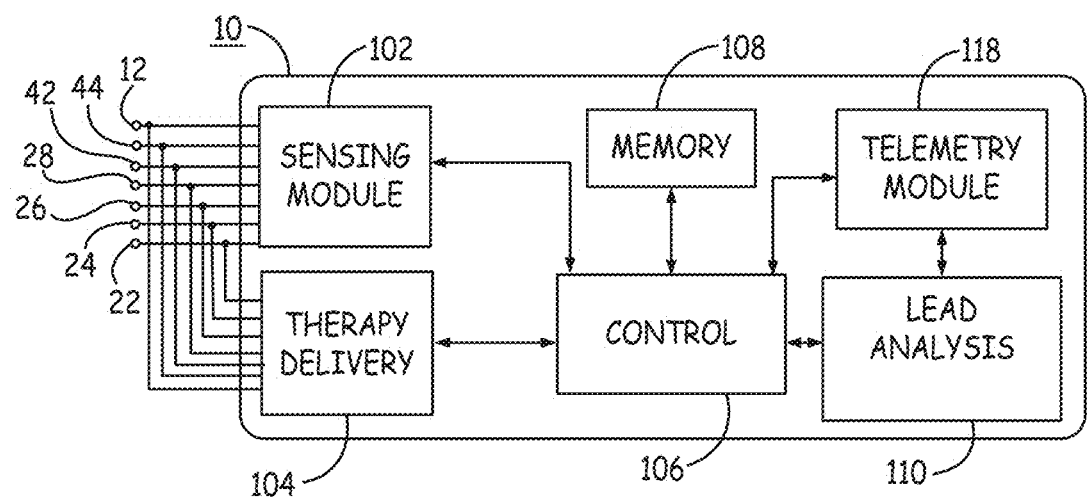
FIG. 2 is a functional block diagram of the system shown in FIG. 1 according to one embodiment.

FIG. 2 is a functional block diagram of IMD 10 according to one embodiment. IMD 10 includes a sensing module 102, a therapy delivery module 104, a control unit 106 and associated memory 108, a lead analysis module 110, and telemetry module 118. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Sensing module 102 receives cardiac electrical signals from electrodes carried by leads 20 for sensing cardiac events attendant to the depolarization of myocardial tissue, e.g. P-waves and R-waves. Sensing module 102 may include a switch module for selectively coupling electrodes 22, 24, 26, 28, 42, 44, and housing electrode 12 to sensing module 102 in order to monitor electrical activity of heart 16. The switch module may include a switch array, switch matrix, multiplexer, or any other type of switching device suitable to selectively couple electrodes to sensing module 102. In some examples, control unit 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, 42, 44 and housing 12 to detect electrical activity of a particular chamber of heart 16, e.g. an atrial sensing channel and a ventricular sensing channel. Each sensing channel may comprise a sense amplifier that outputs an indication to control unit 106 in response to sensing of a cardiac depolarization, in the respective chamber of heart 16. In this manner, control unit 106 may receive sense event signals corresponding to the occurrence of sensed R-waves and P-waves in the respective chambers of heart 16. Sensing module 102 may further include digital signal processing circuitry for providing control unit 106 and/or lead analysis 110 with digitized EGM signals, which may be used for cardiac rhythm discrimination and for lead analysis to detect lead dislodgement by module 110.

Memory 108 may include computer-readable instructions that, when executed by control unit 106 and lead analysis module 110, cause IMD 10 to perform various functions attributed throughout this disclosure to IMD 10, control module 106 and lead analysis module 110. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Control unit 106 may include any one or more of a microprocessor, a controller, a digital signal processor (DSP), an application specific integrated circuit (ASIC), a field-programmable gate array (FPGA), or equivalent discrete or integrated logic circuitry or state machine. In some examples, control unit 106 may include multiple components, such as any combination of one or more microprocessors, one or more controllers, one or more DSPs, one or more ASICs, or one or more FPGAs, as well as other discrete or integrated logic circuitry or state machines. The functions attributed to control unit 106 herein may be embodied as software, firmware, hardware or any combination thereof. Lead analysis module 110 may be implemented as a portion of control unit 106. In one example, lead analysis module 110 may, at least in part, be stored or encoded as instructions in memory 108 that are executed by control unit 106.

Control unit 106 includes a therapy control unit that controls therapy delivery module 104 to deliver electrical stimulation therapy, e.g., cardiac pacing, anti-tachyarrhythmia therapy, or shock pulses, to heart 16 according to a selected one or more therapy programs, which may be stored in memory 108. Therapy delivery module 104 is electrically coupled to electrodes 22, 24, 26, 28, 42, 44 and housing electrode 12 (all of which are shown in FIG. 1). Therapy delivery module 104 is configured to generate and deliver electrical stimulation therapy to heart 16 via selected combinations of electrodes 22, 24, 26, 28, 42, 44, and housing electrode 12.

Memory 108 stores intervals, counters, or other data used by control unit 106 to control the delivery of pacing pulses by therapy delivery module 104. Such data may include intervals and counters used by control unit 106 to control the delivery of pacing pulses to heart 16. The intervals and/or counters are, in some examples, used by control unit 106 to control the timing of delivery of pacing pulses relative to an intrinsic or paced event in another chamber. Memory 108 also stores intervals for controlling cardiac sensing functions such as blanking intervals and refractory sensing intervals and counters for counting sensed events for detecting cardiac rhythm episodes. Events sensed by sense amplifiers included in sensing module 102 are identified in part based on their occurrence outside a blanking interval and inside or outside of a refractory sensing interval. Events that occur within predetermined interval ranges are counted for detecting cardiac rhythms. According to embodiments described herein, sensing module 102, memory 108, control unit 106 and lead analysis module 110 are configured to use timers and counters for measuring sensed event intervals and determining event patterns for use in detecting possible lead dislodgement.

Lead analysis module 110 may receives analog and/or digitized EGM signals and sensed event signals corresponding to sensed R-waves and P-waves from sensing module 102 for use in identifying possible lead dislodgement or dislocation. As will be described herein, lead dislodgement detection may require a predetermined number of event interval patterns that include a short interval followed by a long interval and required signal amplitude criteria to be met.

Control unit 106 may respond to a lead dislodgement identified by lead analysis module 110 by generating a patient or clinician alert, which may be transmitted by telemetry module 118. Control unit 106 may additionally respond to a possible lead dislodgement by adjusting cardiac rhythm episode detection criteria and/or adjusting the control of therapy delivery module 104 to avoid inappropriate delivery or withholding of a therapy.

Telemetry module 118 is used to communicate with external device 30, for transmitting data accumulated by IMD 10 and for receiving interrogation and programming commands from external device 30. Under the control of control unit 106, telemetry module 118 transmits an alert to notify a clinician and/or the patient that IMD 10 has detected a possible lead dislodgement. This alert enables the clinician to perform additional testing to confirm the dislodgement and intervene if necessary to reposition or replace the lead. In other embodiments, IMD 10 may be equipped with alert circuitry configured to emit a sensory alert perceptible by the patient, e.g. a vibration or an audible tone, under the control of control unit 106.

Figure 3:
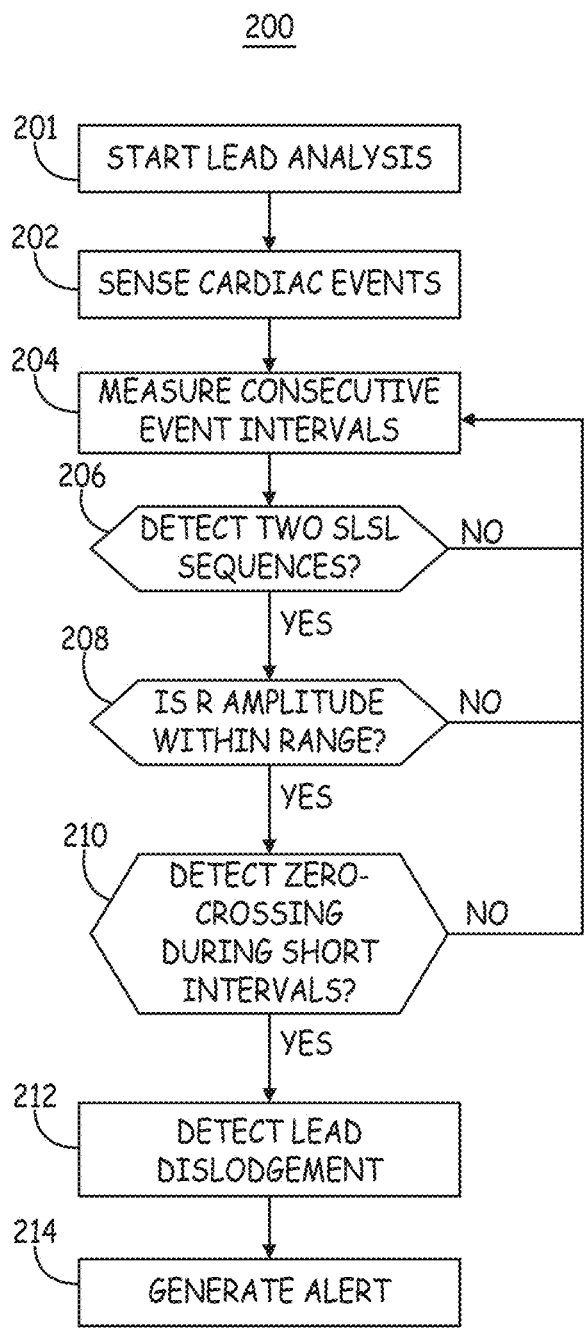
FIG. 3 is a flow chart of a method for detecting lead dislodgement according to one embodiment.

FIG. 3 is a flow chart 200 of a method for detecting lead dislodgement according to one embodiment. Flow chart 200 and other flow charts presented herein are intended to illustrate the functional operation of the medical device system, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

Lead analysis module 110 is enabled at block 201 to begin an analysis for detecting lead dislodgement. Lead analysis may be performed in a substantially continuous basis, in parallel to other operations performing cardiac sensing, e.g. as cardiac signals are sensed for use in cardiac rhythm detection. Alternatively, lead analysis may be performed on a periodic, scheduled basis, e.g. daily, weekly or other periodic interval. In some embodiments, lead analysis may be performed in response to a triggering event. For example, IMD 10 may be enabled to perform automatic loss of capture monitoring, pacing threshold measurements, and/or lead impedance measurements. A loss of capture detection, a change in pacing threshold, or a change in lead impedance may cause control unit 106 to enable lead analysis module to analyze cardiac signals for detecting lead dislodgement, which may be the cause of the change in pacing threshold or lead impedance. In another example, lead analysis module may be enabled to detect lead dislodgement if a threshold number of short intervals are sensed, e.g. a predetermined number of RR intervals falling within a VT or VF detection zone or other predefined short interval range.

At block 202, sensing module 102 is enabled to sense cardiac events from one or more cardiac signals received from selected ones of electrodes 22, 24, 26, 28, 42, 44, and housing electrode 12. The cardiac events are sensed from an EGM signal that is acquired using at least one electrode from a cardiac lead that is being evaluated for lead dislodgement. In an illustrative embodiment, a ventricular EGM signal is acquired using electrodes 22 and 24 of lead 20 for sensing R-waves. At block 204, the intervals between consecutively sensed R-waves, i.e. RR intervals, are measured. It is recognized that cardiac signal sensing may be operating continuously for monitoring the patient's heart rate and rhythm by control unit 106, and sensed event signals and/or measured event intervals may be provided as input to lead analysis module 110.

At block 206, the sensed event intervals, e.g. RR intervals, are monitored to detect an event interval pattern that is characteristic of lead dislodgement but distinguishes lead dislodgement from a tachyarrhythmia event pattern. In one embodiment, control unit 106 determines if two sequences of a short-long-short-long (SLSL) event interval pattern are detected. If the ventricular lead 20 has become dislodged and migrated such that electrodes 22 and 24 are closer to the right atrium, both P-waves and R-waves may be sensed by electrodes 22 and 24. Both the P-waves and the R-waves will be sensed as "R-waves" by sensing module 102 since electrodes 22 and 24 of RV lead 20 will be coupled to a ventricular sensing channel. A P-wave sensed as an R-wave followed by a true R-wave will result in a short, false "RR" interval being measured followed by a long RR interval. The long RR interval may be a true RR interval or it may be an interval between a true R-wave the next P-wave falsely sensed as an R-wave.

In the case of lead dislodgement, an event interval pattern represented by a consecutive sequence of SLSL intervals followed by a second sequence of SLSL intervals is evidence of possible lead dislodgement. The two SLSL sequences may occur consecutively or non-consecutively, but the SLSL interval pattern that occurs within a single sequence are consecutive short and long intervals. Additionally, the two SLSL sequences are required to occur within a predetermined time interval, for example within 10 seconds. It is recognized that in other embodiments different criteria may be established for defining a predetermined number of sequences of a particular event interval pattern that is indicative of lead dislodgement. In general, a criterion for detecting an interval pattern sequence that includes at least one short-long pair or RR intervals is used to detect a first indication of possible lead dislodgement.

A definition of a short interval and a definition of a long interval are established and stored in memory 108 and used by lead analyzer 110 for detecting the SLSL sequences. In one embodiment, a short interval is defined as an interval that is between approximately 120 ms and 250 ms long. The short interval is defined to correspond approximately to an expected P-R interval. The long interval may be defined in ms or as a multiple of the short interval. For example, a long interval may be required to be at least 1.5 times longer than a short interval.

If the required number of sequences of a specified interval pattern is not met at block 206, the process may return to block 204 to continue monitoring event intervals for a lead analysis window of time or until lead analysis module 110 is controlled by control unit 106 to stop lead analysis. If the interval pattern criteria are met at block 206, additional analysis of the ventricular signal is performed to obtain supporting evidence for detection of lead dislodgement.

At block 208, at least one EGM signal amplitude associated with the required event interval pattern is measured. In one embodiment, the sensed R-wave amplitudes of the events defining the detected SLSL sequences are compared to a predetermined amplitude range. If lead dislodgement has occurred, the amplitude of the P-waves falsely sensed as R-waves and the amplitude of the true R-waves are expected to fall in a low to middle amplitude range due to the mislocated lead. The amplitude of the true R-waves sensed by a disloged lead is expected to be lower than the higher quality R-wave signal expected when the lead is properly positioned. The amplitude of the P-wave falsely sensed as an R-wave is expected to be higher than a P-wave would normally appear on a ventricular lead signal when the lead is properly position. The amplitudes of the sensed event signals contributing to the SLSL sequences, therefore, may be required to fall within a predetermine amplitude range, e.g. greater than 0.5 mV and less than 2.5 mV, in order to detect evidence of lead dislodgement. Higher amplitudes may indicate noise or a properly sensed R-wave. The amplitudes of the sensed events defining the short and long intervals may be measured as maximum peak amplitudes of the signal after a sensing threshold crossing.

If the R-wave amplitudes are within the predefined range ("yes" branch of block 208), the lead analysis module 110 determines whether a zero-crossing of the EGM signal occurs between the two sensed cardiac events defining at least one of the short intervals of the SLSL sequences. If no zero-crossing occurs, the short interval may be the result of double sensing of a wide R-wave signal or double sensing of other non-cardiac noise. If a zero-crossing does occur, the signal has returned to baseline between two distinct events, such as a P-wave and an R-wave that may both be sensed as R-waves defining the short intervals.

If all of these criteria are met, i.e. two sequences of SLSL intervals, sensed cardiac event amplitudes within the predefined amplitude range, and a zero-crossing during at least one of the short intervals, lead dislodgement is detected at block 212. For example, dislodgement of the ventricular lead 20 is detected when the ventricular EGM signal meets these criteria. A patient or clinician alert may be generated at block 214 as described previously. Additionally, an adjustment to the sensing and/or detection and therapy delivery operations of the IMD may be made in response to lead dislodgement detection as will be further described below in conjunction with the examples shown in FIG. 4 and FIG. 5.

In some embodiments, detection of lead dislodgement based on EGM event interval patterns and signal amplitudes may trigger additional testing to be performed by IMD 10 to confirm the dislodgement detection. For example, a lead impedance measurement, pacing threshold measurement, or pacing capture detection may be performed to verify that a change in the lead position is likely.

Figure 4:
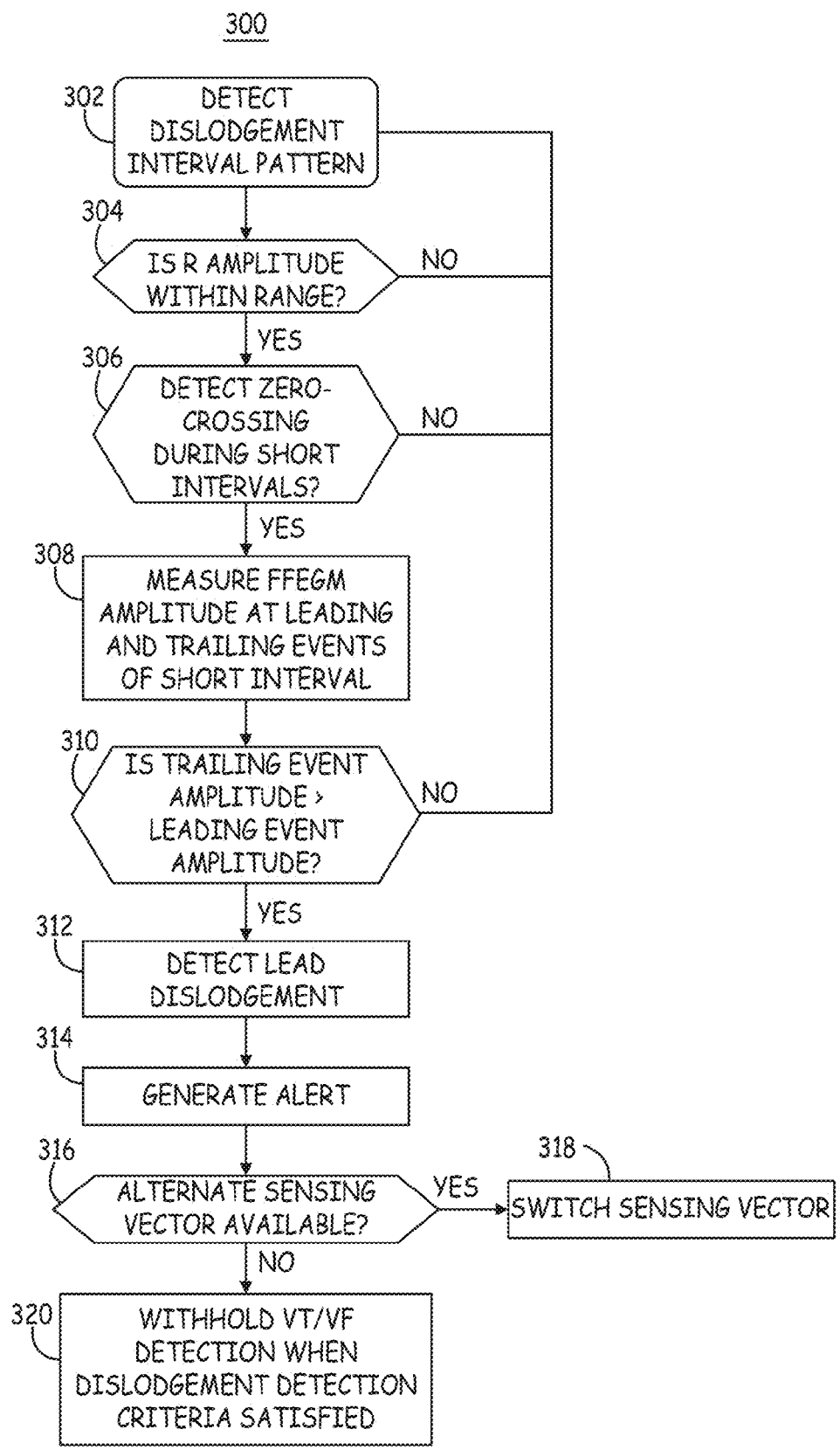
FIG. 4 is a flow chart of a method for detecting lead dislodgement according to an alternative embodiment.

FIG. 4 is a flow chart 300 of a method for detecting lead dislodgement according to an alternative embodiment. The method 300 may operate continuously for detecting possible lead dislodgement whenever sensing module 102 is operating or performed on a scheduled and/or triggered basis as described previously. At block 302, a lead dislodgement interval pattern is detected. A lead dislodgement interval pattern is an event interval pattern including at least one short-long interval pattern. The interval pattern may include two sequences of consecutive SLSL intervals occurring within 10 seconds of each other as described above. Other interval patterns including a different number of consecutive short-long intervals or a different number of sequences of patterns including short-long interval patterns or a different time interval within which the sequence(s) are detected may be defined.

When the required interval pattern is detected at block 302, the sensed event amplitudes, i.e. the sensed "R-wave" amplitudes, defining the short-long intervals are measured and compared to a detection amplitude range, e.g. between approximately 0.5 mV and 2.5 mV. The R-wave amplitudes defining only the short interval(s) may be measured and compared to the defined amplitude range. Alternatively all or any subset of the sensed cardiac events defining the S-L intervals may be measured to determine if the amplitudes fall within the required range. If the amplitude requirement is met, the process continues to block 306. Otherwise the process may return to block 302 to wait for the next lead dislodgement interval pattern to be detected.

If the sensed event amplitude is within the predefined range, the lead analysis module determines if a zero crossing or a return to baseline occurs during the short intervals at bloc 306. If the signal returns to baseline, indicating two distinct sensed event as opposed to a wide QRS or other noise signal being sensed twice, the process advances to block 308.

At block 308, a far-field (FF) EGM signal is sensed using a different set of electrodes than the EGM signal used for detecting the dislodgement interval pattern. For example, if the ventricular electrodes 22 and 24 are used to sense a near-field ventricular EGM signal used to detect a dislodgement event interval pattern, a FF EGM signal may be sensed between ring electrode 24 and coil electrode 44, between coil electrode 44 and housing electrode 12, or between coil electrodes 42 and 44. A short interval is identified on the far-field EGM signal. In some embodiments, the FF EGM signal is recorded simultaneously with the ventricular signal so as to obtain a FF EGM signal over the same SLSL sequences identified on the ventricular signal. Alternatively, short intervals may be identified on the FF EGM subsequent to detecting the required SLSL sequences on the ventricular signal, but which also correspond to short intervals on the ventricular EGM signal.

The amplitude of the FF EGM signal at the time of a sensed event ending, i.e. trailing, a short interval is compared to the FF EGM amplitude occurring at the beginning, i.e. leading, the short interval. The leading and trailing FF EGM event amplitudes for one or more of the short intervals occurring in a SLSL sequence (or other pattern sequence used to detect possible lead dislodgement) may be measured at block 308.

If the leading event of a short interval is actually a P-wave and the trailing event an R-wave, the true R-wave amplitude is expected to be substantially greater than the true P-wave on the FF EGM signal. In one example, if the FF EGM event amplitude corresponding in time to the trailing event is at least 1.5 times the FF EGM amplitude corresponding in time to the leading event, the leading event is likely a true P-wave falsely sensed as an R-wave on the ventricular EGM signal. This FF EGM signal evidence of a true P-wave supports a detection of lead dislodgement. Accordingly, if the trailing event amplitude exceeds the leading event amplitude by a required amount, as determined at block 310, lead dislodgement is detected at block 312. An alert is generated in response to detecting lead dislodgement at block 314, as described previously.

In an alternative embodiment, if events are sensed from a FF EGM signal by sensing module 102, the timing of events sensed on the FF EGM may be compared to the timing of events sensed on the near-field EGM signal. An R-wave sensed on the FF EGM signal is expected to correspond in time with (i.e. be within a short time window of) the trailing R-wave of a short interval sensed on the near-field EGM. There would be no sensed event on the FF EGM signal corresponding in time to a P-wave falsely sensed as an R-wave on the near-field EGM signal. As such, the absence of a sensed event on the FF EGM signal corresponding in time to the leading sensed event of a short interval on the near-field EGM signal would support a lead dislodgement detection.

If the FF EGM signal amplitudes (or sensed events) corresponding in time to a leading short interval event and a trailing short interval event do not meet the criteria applied at decision block 310, the lead analysis process may return to block 302 until a lead dislodgement event interval pattern is detected again.

In some embodiments, lead dislodgement detection may alter how the IMD detects a cardiac rhythm episode and/or the decision to deliver a therapy. For example, after detecting lead dislodgement, the control unit 106 may determine at block 316 if an alternative sensing vector is available that could be substituted for the sensing vector that had been utilized on the dislodged lead. Control unit 106 may control switching circuitry in sensing module 102 to select a different sensing vector at block 318 for obtaining a cardiac EGM signal provided to the sensing channel previously coupled to a sensing vector on the dislodged lead. For example, if an RV lead is detected as being dislodged, and a coronary sinus lead is available, the sensing module may be coupled to electrodes carried by the coronary sinus lead for sensing ventricular events.

In some examples, an alternative sensing vector may be a far-field sensing vector that is substituted for the sensing vector negatively impacted by lead dislodgement. In other embodiments, an alternative sensing vector may be a near-field sensing vector that is substituted. The alternative sensing vector selected for substitution for a sensing vector that is no longer reliable due to lead dislodgement detection will depend on the lead and electrode configuration used and the sensing requirements for the particular detection algorithm implemented in the IMD.

If no other suitable sensing vector is available (as determined at block 316), or instead of selecting a substitute sensing vector, the control unit 106 may alter the cardiac rhythm episode detection algorithm by withholding a VT or VF detection as long as lead dislodgement detection criteria are satisfied at block 320. Under this altered operating condition, if VT or VF detection criteria are met that would normally result in a VT or VF therapy being delivered, the detection may be withheld, thereby withholding the therapy, as long as lead dislodgement is being detected. If lead dislodgement detection criteria are no longer met, and VT or VF detection criteria are still being met (or are met again at a future time), the cardiac episode detection may be made and a scheduled therapy delivered.

Figure 5:
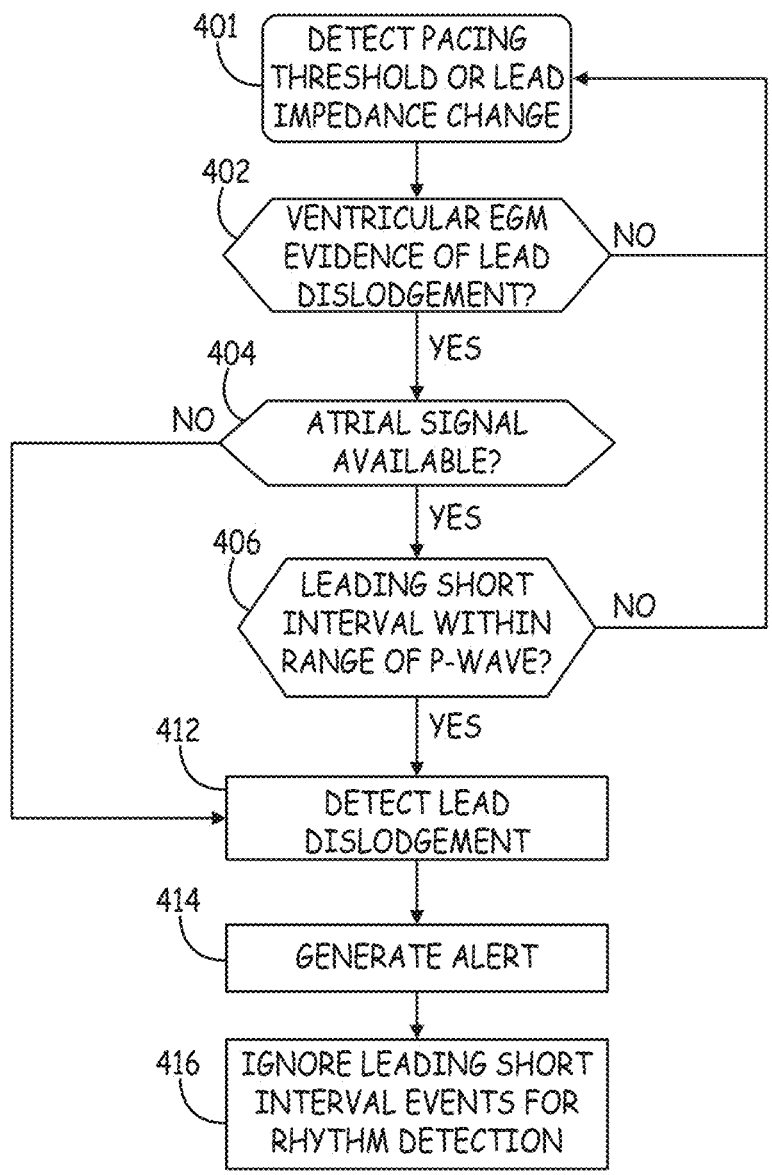
FIG. 5 is a flow chart of a method for detecting lead dislodgement according to yet another embodiment.

FIG. 5 is a flow chart 400 of a method for detecting lead dislodgement according to yet another embodiment. As mentioned previously, lead analysis may be performed in response to detecting a triggering condition at block 401, such as a change in pacing threshold or lead impedance. Alternatively, the process shown by flow chart 400 may be performed on a scheduled or substantially continuous basis.

At block 402, the ventricular EGM signal is evaluated to detect evidence for lead dislodgement. The ventricular EGM evaluation may include detection of a predefined event interval pattern, event amplitudes within a predefined amplitude range, and a zero crossing between events defining a short interval, as described above.

If the ventricular EGM signal analysis supports a lead dislodgement detection ("yes" branch of block 402) and no atrial EGM signal is available (block 404), a lead dislodgement detection is made at block 412 based on the ventricular EGM signal analysis. If an atrial EGM signal is available, the timing of the leading events of the short intervals identified on the ventricular EGM relative to an atrial event is determined at block 406. The atrial event may be an event sensed as a P-wave on the atrial EGM signal or an atrial pacing pulse.

If the leading short interval events sensed from the ventricular EGM signal are within 50 ms, for example, of an atrial, the leading events of the short intervals are presumed to be atrial events not R-waves. Lead dislodgement is detected at block 412 in response to the short interval leading events being within a predetermined time interval from an atrial event.

At block 414 a patient or clinician alert is generated. In some embodiments, in addition to generating an alert, the leading events of the short intervals are ignored by control unit 106 in a cardiac rhythm detection algorithm. The leading events of the short intervals may be ignored and ventricular EGM event intervals recalculated for use in detecting and classifying cardiac rhythm episodes.

In the examples shown in FIGS. 3, 4 and 5, particular operations are shown in a given order and combination. It is recognized that the various operations described in conjunction with flow charts 200, 300 and 400 could be performed in a different order than that shown and the various operations may be performed in other combinations than the combinations shown and described herein. Some operations may be omitted and some may be added to the methods shown by flow charts 200, 300 and 400.

Figure 6:
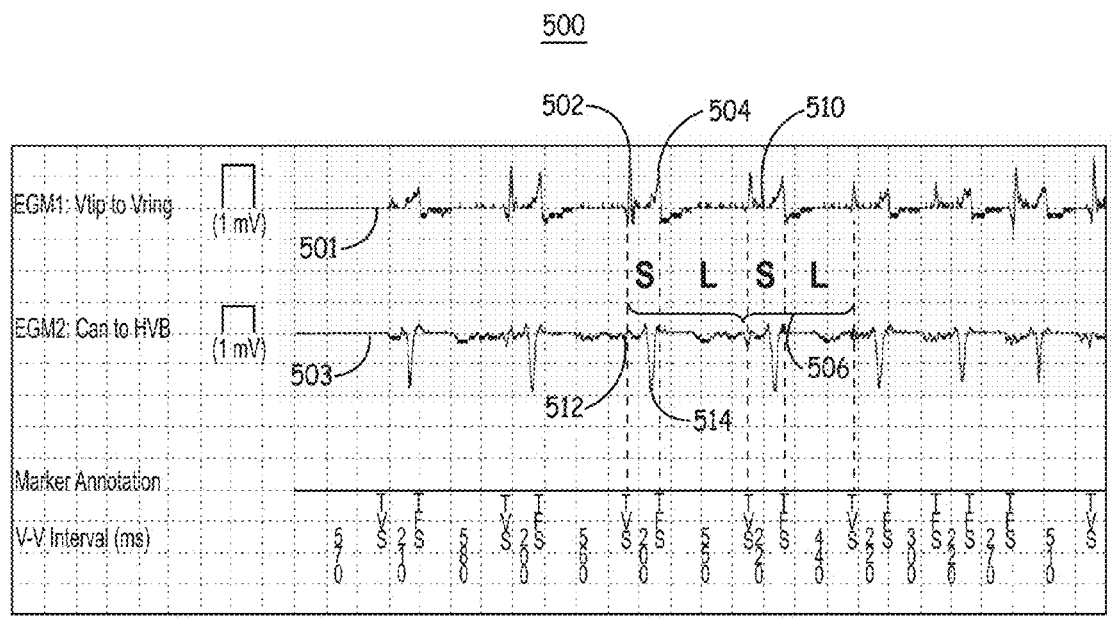
FIG. 6 is a sample recording of EGM signals recorded from a dislodged ventricular lead.
Figure 6:
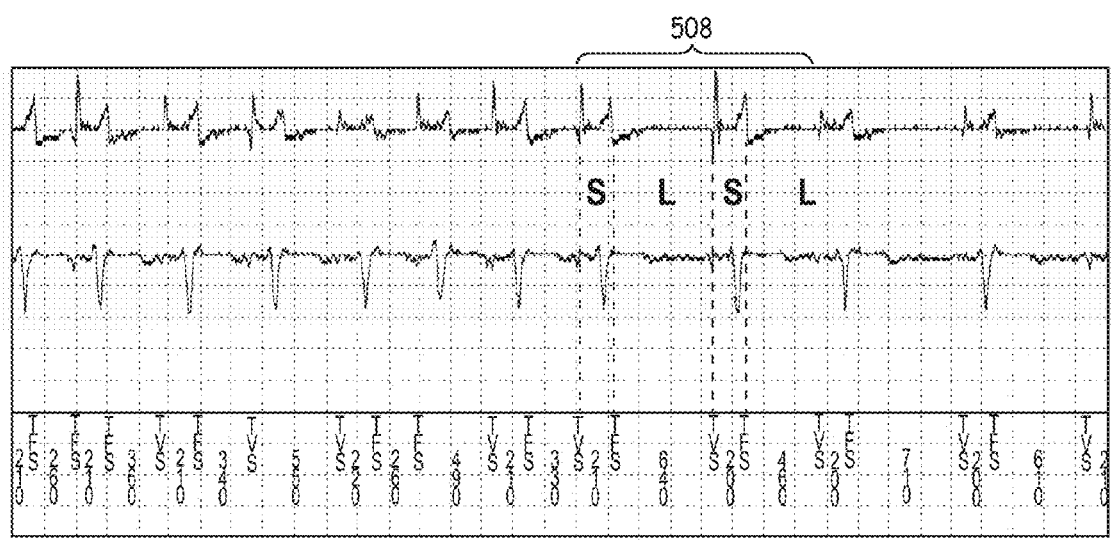

FIG. 6 is a sample recording 500 of EGM signals recorded from a dislodged ventricular lead. EGM signal characteristics typifying a lead dislodgement situation, e.g. due to "Twiddler's" syndrome, are distinguished from EGM characteristics typifying VT or VF. For example, two sequences 506 and 508 of a SLSL interval pattern occurring within approximately 10 seconds are identified. When true VT or VF is occurring, these SLSL sequences are not expected. Instead, multiple consecutive short intervals are more likely to occur as opposed to the alternating SLSL pattern.

Additionally, both the leading and trailing events 502 and 504 of a short interval will have a relatively low level amplitude, e.g. between 0.5 and 2.5 mV. When the lead is properly positioned, sensed R-waves typically have a relatively higher amplitude, e.g. greater than 2.5 mV. The amplitudes of the leading and trailing events 502 and 504 defining short intervals and/or leading and trailing events defining long intervals in the SLSL pattern, labeled in FIG. 6 by "S" and "L" notations, can be compared to a predefined range or compared to a historically measured sensed R-wave amplitude. The amplitude of true R-waves is expected to be decreased when lead dislodgement occurs as compared to R-waves sensed by a properly placed lead. If sensed "R-waves" present a consistently lower amplitude than in the past, this change in amplitude is evidence of lead dislodgment.

A zero-crossing or return to baseline 510 during the short intervals is evidence of two distinct events defining the short intervals. In contrast, if no zero-crossing or return to baseline during the short intervals is detected, the short intervals could represent double-sensing of a wide QRS signal. Requiring a zero-crossing or return to baseline during the short intervals in order to detect lead dislodgement, therefore, avoids detecting lead dislodgement in the presence of R-wave oversensing.

If a far-field EGM signal 503 is available, a comparison may be made between the peak amplitudes 512 and 514 of the FF EGM signal at the times, or within a short window, of the short interval leading and trailing ventricular EGM sensed events 502 and 504. The trailing peak amplitude 514 of the FF EGM signal 503 is expected to be significantly greater, e.g. at least 1.5 times greater, than the leading peak amplitude 512 because the leading event 512 is a true P-wave and the trailing event 514 is a true R-wave. If FF EGM event amplitudes 512 and 514 are similar, or if leading event amplitude 512 is greater than trailing event amplitude 514, a lead dislodgement detection is not supported.

Accordingly, by identifying EGM interval pattern and amplitude characteristics that reliably distinguish lead dislodgement from tachyarrhthmia episodes, lead dislodgement can be detected, allowing early intervention to reposition or replace the lead. Inappropriate therapy delivery or therapy withholding due to improper sensing can potentially be avoided. A near-field EGM signal may be examined alone for lead dislodgement characteristics or a combination of the near-field EGM signal and a FF EGM signal and/or an EGM signal in a different heart chamber may be examined.

It is further recognized that while the illustrative embodiments referred to herein relate to detection of ventricular lead dislodgement, the methods may be adapted to detecting atrial lead dislodgement or left ventricular lead dislodgement. For example, an EGM signal sensed from an atrial lead that has migrated toward or into the ventricle may present similar characteristics as described and presented in FIG. 6. Likewise, a coronary sinus lead that has been positioned for sensing an EGM signal from the left ventricle may migrate toward the left atrium and present similar changes as those discussed in conjunction with FIG. 6 typifying ventricular lead dislodgment or dislocation.

Thus, a system and method for detecting lead dislodgement have been presented in the foregoing description with reference to specific embodiments. It is appreciated that various modifications to the referenced embodiments may be made without departing from the scope of the disclosure as set forth in the following claims.

The invention claimed is:

1. A medical device system for detecting lead dislodgement, comprising:
   a plurality of electrodes;
   a cardiac lead carrying at least one of the plurality of electrodes;
   a sensing module for receiving a first cardiac electrical signal using a first pair of the plurality of electrodes for sensing cardiac electrical events, the first pair comprising the at least one electrode of the plurality of electrodes carried by the cardiac lead; and
   a control unit configured to:
      measure intervals between the sensed cardiac electrical events for detecting short event intervals shorter than a first event interval threshold and long event intervals longer than a second event interval threshold, the second event interval threshold longer than the first event interval threshold;
      detect an event interval pattern from the first cardiac electrical signal, the event interval pattern comprising at least one short event interval consecutively followed by a long event interval of the measured intervals;
      responsive to detecting the event interval pattern, measure an amplitude of at least one of the sensed cardiac electrical events that is associated with the at least one detected short event interval;
      compare the amplitude to a voltage range requirement, and
      detect dislodgement of the cardiac lead in response to detecting the event interval pattern and the amplitude of the at least one of the sensed cardiac electrical events that is associated with the at least one detected short event interval being within the voltage range requirement, wherein measuring the amplitude comprises measuring a first amplitude of a first one of the sensed cardiac electrical events that is a leading cardiac event of the at least one short event interval and measuring a second amplitude of a second one of the sensed cardiac electrical events that is a trailing cardiac event of the at least one short event interval, and wherein the control module is further configured to compare both of the first amplitude and the second amplitude to the voltage range requirement, and detect the dislodgment in response to both the first amplitude and the second amplitude being within the voltage range requirement.

2. The system of claim 1, wherein detecting the event interval pattern comprises detecting a plurality of sequences comprising a short-long-short-long event interval pattern.

3. The system of claim 1, wherein the sensing module is enabled to receive a second cardiac electrical signal using a second pair of electrodes different than the first pair of electrodes and to sense a cardiac event from the second cardiac electrical signal; and
   the control unit configured to detect the lead dislodgment in response to the cardiac event from the second cardiac electrical signal being within a predetermined time range of one of the sensed cardiac electrical events of the first cardiac electrical signal that is a leading cardiac event of the at least one short interval.

4. The system of claim 1, further comprising means for generating an alert controlled by the control unit to generate the alert in response to detecting the lead dislodgment.

5. The system of claim 1, wherein the control unit is further configured to:
   detect a cardiac rhythm episode in response to the sensed cardiac events; and
   during cardiac rhythm episode detection, ignore one of the sensed cardiac electrical events of the first cardiac electrical signal that is a leading cardiac event of the at least one short event interval in response to detecting the lead dislodgement.

6. The system of claim 1, further comprising a therapy delivery module for delivering a therapy in response to a cardiac rhythm episode detection,
   the control unit configured to detect the cardiac rhythm episode in response to the sensed cardiac electrical events and control the therapy delivery module to withhold the therapy as long as the lead dislodgement detection is being made.

7. The system of claim 1, further comprising switching circuitry to selectively couple selected ones of the plurality of electrodes to the sensing module,
   the control unit configured to control the switching circuitry to selectively couple a second pair of electrodes, different than the first pair of electrodes, to the sensing module for sensing cardiac event signals in response to detecting lead dislodgement.

8. A medical device system for detecting lead dislodgement, comprising:
   a plurality of electrodes;
   a cardiac lead carrying at least one of the plurality of electrodes;
   a sensing module for receiving a first cardiac electrical signal using a first pair of the plurality of electrodes for sensing cardiac electrical events, the first pair comprising the at least one electrode of the plurality of electrodes carried by the cardiac lead; and
   a control unit configured to:
      measure intervals between the sensed cardiac electrical events for detecting short event intervals shorter than a first event interval threshold and long event intervals longer than a second event interval threshold, the second event interval threshold longer than the first event interval threshold;
      detect an event interval pattern from the first cardiac electrical signal, the event interval pattern comprising at least one short event interval consecutively followed by a long event interval of the measured intervals;
      responsive to detecting the event interval pattern, measure an amplitude of at least one of the sensed cardiac electrical events that is associated with the at least one detected short event interval;
      compare the amplitude to a voltage range requirement, and
      detect dislodgement of the cardiac lead in response to detecting the event interval pattern and the amplitude of the at least one of the sensed cardiac electrical events that is associated with the at least one detected short event interval being within the voltage range requirement, wherein the control module is further configured to:
   detect a zero crossing of the first cardiac electrical signal during the at least one short event interval, and detect the dislodgment if the zero crossing of the first cardiac electrical signal is detected during the short interval.

9. A medical device system for detecting lead dislodgement, comprising:
   a plurality of electrodes;
   a cardiac lead carrying at least one of the plurality of electrodes;
   a sensing module for receiving a first cardiac electrical signal using a first pair of the plurality of electrodes for sensing cardiac electrical events , the first pair comprising the at least one electrode of the plurality of electrodes carried by the cardiac lead; and
   a control unit configured to:
      measure intervals between the sensed cardiac electrical events for detecting short event intervals shorter than a first event interval threshold and long event intervals longer than a second event interval threshold, the second event interval threshold longer than the first event interval threshold;
      detect an event interval pattern from the first cardiac electrical signal, the event interval pattern comprising at least one short event interval consecutively followed by a long event interval of the measured intervals;
      responsive to detecting the event interval pattern, measure an amplitude of at least one of the sensed cardiac electrical events that is associated with the at least one detected short event interval;
      compare the amplitude to a voltage range requirement, and
      detect dislodgement of the cardiac lead in response to detecting the event interval pattern and the amplitude of the at least one of the sensed cardiac electrical events that is associated with the at least one detected short event interval being within the voltage range requirement, wherein the sensing module is enabled to receive a second cardiac electrical signal using a second pair of electrodes of the plurality of electrodes different than the first pair of electrodes;
   the control unit further configured to:
      measure a first amplitude of the second cardiac electrical signal corresponding to one of the sensed cardiac event signals that is a leading cardiac event of the at least one short event interval;
      measure a second amplitude of the second cardiac signal corresponding to another of the sensed cardiac event signals that is a trailing cardiac event of the at least one short event interval;
      compare the first amplitude to the second amplitude; and
      detect the lead dislodgment in response to the second amplitude being greater than the first amplitude.

* * * * *